US009804065B2

(12) United States Patent
Suzuki et al.

(10) Patent No.: US 9,804,065 B2
(45) Date of Patent: Oct. 31, 2017

(54) SYSTEM FOR PRETREATING SAMPLE (71) Applicant: HITACHI HIGH-TECHNOLOGIES CORPORATION, Tokyo (JP)

(72) Inventors: Iwao Suzuki, Tokyo (JP); Tadao Shimizu, Tokyo (JP); Shigeru Yano, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 404 days.

(21) Appl. No.: 14/379,787

(22) PCT Filed: Feb. 19, 2013

(86) PCT No.: PCT/JP2013/054037
§ 371 (c)(1),
(2) Date: Aug. 20, 2014

(87) PCT Pub. No.: WO2013/129191
PCT Pub. Date: Sep. 6, 2013

(65) Prior Publication Data
US 2015/0031143 A1    Jan. 29, 2015

(30) Foreign Application Priority Data

Feb. 27, 2012    (JP) ................ 2012-040740

(51) Int. Cl.
*G01N 1/28*    (2006.01)
*G01N 35/00*    (2006.01)
*G01N 35/10*    (2006.01)

(52) U.S. Cl.
CPC .......... *G01N 1/28* (2013.01); *G01N 35/0092* (2013.01); *G01N 35/1016* (2013.01);
(Continued)

(58) Field of Classification Search
CPC ........................................... G01N 1/28
(Continued)

(56) References Cited

U.S. PATENT DOCUMENTS 4,731,225 A * 3/1988 Wakatake .............. G01N 35/02
422/562
5,314,825 A * 5/1994 Weyrauch ........ G01N 35/00663
356/246

(Continued)

FOREIGN PATENT DOCUMENTS

JP        63-122959 A    5/1988
JP          4-3355 U     1/1992
(Continued)

OTHER PUBLICATIONS

International Preliminary Report on Patentability received in International Application No. PCT/JP2013/054037 dated Sep. 12, 2014.

*Primary Examiner* — Christine T Mui
*Assistant Examiner* — Emily Berkeley
(74) *Attorney, Agent, or Firm* — Mattingly & Malur, PC (57) ABSTRACT

A sample pretreatment system is equipped with a pipetting device for pipetting multiple primary samples to make multiple aliquot samples. The sample volume expected to be held in a test tube is set as a minimum guaranteed volume for each type of test tube; and a minimum guaranteed volume value is set for each type of the test tubes. A cumulative totaling unit adds up cumulatively the aliquot volumes of the aliquot samples based on pipetting request information with regard to the supplied test tubes. A reading unit reads the minimum guaranteed volume of the supplied test tube; and an aliquot sample preparation unit compares the minimum guaranteed volume successively with the cumulative total values of the aliquot volumes of the aliquot samples, and causes a pipetting device to pipette a maximum (Continued)

number of the aliquot samples in a manner not exceeding the minimum guaranteed volume.

5 Claims, 7 Drawing Sheets

(52) U.S. Cl.
CPC ............... *G01N 2035/0094* (2013.01); *G01N 2035/1032* (2013.01); *Y10T 436/2575* (2015.01)

(58) Field of Classification Search
USPC ......................................................... 436/180
See application file for complete search history.

(56) References Cited

U.S. PATENT DOCUMENTS

| 2004/0005245 A1* | 1/2004 | Watson | B65G 47/1471 |
| | | | 422/65 |
| 2006/0153737 A1* | 7/2006 | Saito | G01N 35/0092 |
| | | | 422/68.1 |

FOREIGN PATENT DOCUMENTS

| JP | 11-118809 A | 4/1999 |
| JP | 2003-083991 A | 3/2003 |
| JP | 2007-040932 A | 2/2007 |
| JP | 2008-292393 A | 12/2008 |

\* cited by examiner

| MANUFACTURER | PRODUCT NAME | VOLUME OF COLLECTED BLOOD | MINIMUM GUARANTEED VOLUME |
|---|---|---|---|
| A CORP. | ○○○ | 2 mL | 1000 μL |
| A CORP. | ○○○ | 3 mL | 1500 μL |
| A CORP. | ○○○ | 5 mL | 2500 μL |
| A CORP. | ○○○ | 7 mL | 3500 μL |
| A CORP. | ○○○ | 10 mL | 5000 μL |
| B CORP. | △△△ | 5 mL | 2500 μL |
| B CORP. | △△△ | 7 mL | 3500 μL |
| B CORP. | ▽▽▽ | 7 mL | 3500 μL |
| B CORP. | ▽▽▽ | 10 mL | 5000 μL |
| C CORP. | ××× | 7 mL | 3500 μL |

| ALARM LIST | | | |
|---|---|---|---|
| NUMBER | MODULE NAME | LEVEL | MESSAGE |
| 123-123456 | SAMPLE LOADING UNIT | CAUTION | SAMPLE YET TO ARRIVE |
| | | | |
| | | | |
| | | | |

| EXPLANATION AND COUNTERMEASURES | |
|---|---|
| NUMBER | 123-123456 |
| LEVEL | CAUTION |
| EXPLANATION | THE SAMPLE HAS NOT ARRIVED YET. |
| COUNTERMEASURES | THE STANDBY TIME HAS ELAPSED BUT THE PRIMARY SAMPLE NECESSARY FOR PIPETTING HAS NOT ARRIVED. LOAD THE PRIMARY SAMPLE. IF THE PRIMARY SAMPLE IS NOT FOUND, COLLECT AN ADDITIONAL BLOOD SAMPLE AND LOAD IT INTO THE SYSTEM. |

SYSTEM FOR PRETREATING SAMPLE

TECHNICAL FIELD

The present invention relates to a system for pretreating samples for clinical laboratory tests.

BACKGROUND ART

In the field of clinical laboratory tests, a system is used to perform pretreatments such as the pipetting of a primary sample to make aliquot samples prior to analytical processing including biochemical analyses and immunoassays of blood, urine and other samples. For such pretreatment systems, the volume of collected samples has increased in recent years along with an increasing number of items to be analyzed, and multiple primary samples have come to be collected. As a result, there has been a growing need for the capability to prepare aliquot samples from multiple primary samples. This need is met, for example, by an apparatus that transfers multiple primary samples on a sample transfer rack so as to pipette the multiple primary samples to make multiple aliquot samples (see Patent Literature 1).

PRIOR ART LITERATURE

Patent Literature

Patent Literature 1: JP-2007-040932-A

SUMMARY OF THE INVENTION

Problem to be Solved by the Invention

The apparatus disclosed in the above-cited Patent Literature 1 involves transferring all multiple primary samples on a single sample transfer rack, with the management of the primary samples being dependent on information about the sample transfer rack.

However, where the centrifuge process is performed before execution of the pipetting process on the pretreatment apparatus for example, there are restrictions on the number of samples that can be loaded into a centrifugal separator. For this reason, it obviously happens that not all containers of the same sample (all having the same identification barcode) can be loaded into the centrifugal separator if the free space of the latter is limited. Although the next centrifuge process is conceivably awaited so that the multiple containers of the same sample may be loaded altogether into the centrifugal separator, taking such steps all the time will lead to inefficient processing. It is thus desired that multiple containers of the same sample be treated separately in various processes of the pretreatment system and that a desired number of aliquot samples still be prepared ultimately from these primary sample containers.

However, if the containers of a primary sample are handled separately, there is no knowing how many containers of the same primary sample would be subsequently transferred to the pipetting process (i.e., the total volume of the sample in question is unknown). It is thus impossible to determine how many aliquot samples are to be prepared from the transferred primary samples, and appropriate preparation of the aliquot samples remains difficult.

It is therefore an object of the present invention to provide a system for pretreating samples whereby multiple aliquot samples can be prepared from multiple primary samples that have been transferred separately.

Means for Solving the Problem

In achieving the object above, the present invention provides setting a minimum guaranteed volume for each test tube type (i.e., the volume of a sample expected to be held as a minimum in a test tube), and preparing a maximum number of aliquot samples in a manner not exceeding the minimum guaranteed volume based on the minimum guaranteed volume and on an aliquot volume of each requested aliquot sample.

Effect of the Invention

According to the present invention, multiple aliquot samples can be prepared suitably from multiple primary samples transferred separately.

MODE FOR CARRYING OUT THE INVENTION

Figure 7:
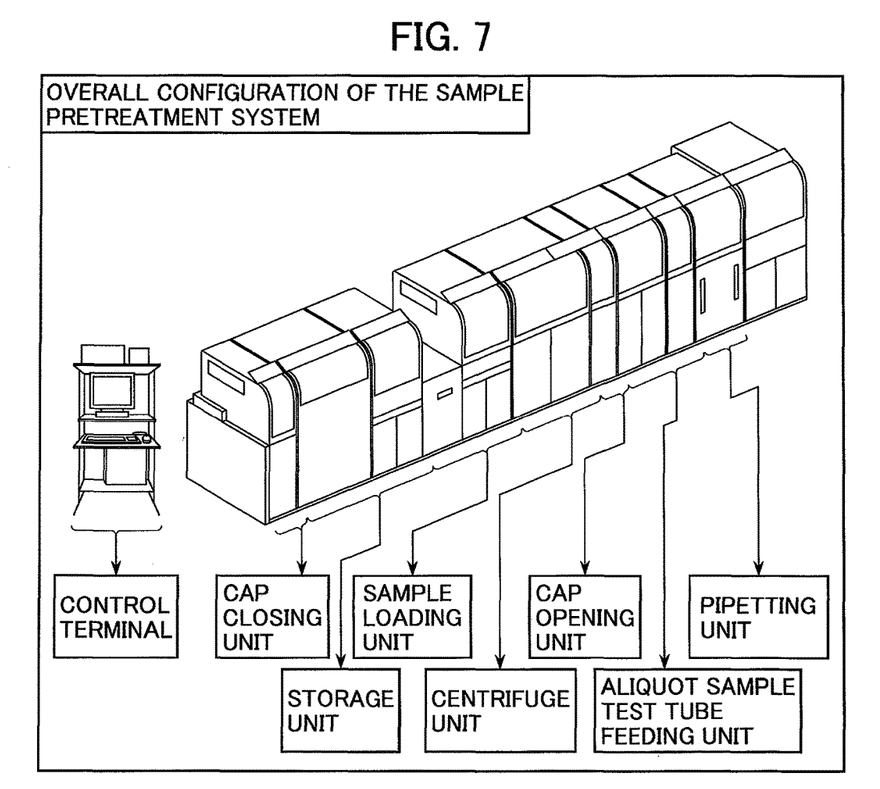
FIG. 7 is an illustration depicting an overall configuration of the sample pretreatment system according to the present invention.
Figure 8:
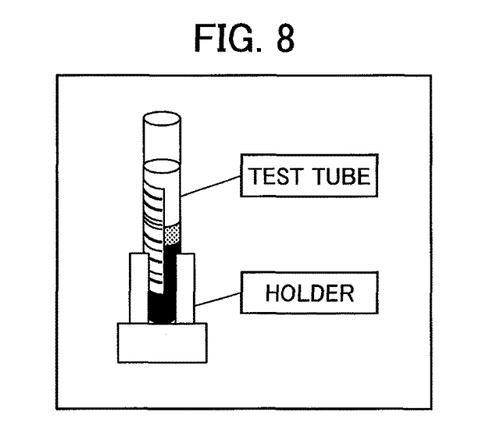
FIG. 8 is an illustration depicting a test tube along with a holder for tube transfer purposes, the test tube being used by the sample pretreatment system according to the present invention.

The present invention provides a system and a method for efficiently preparing multiple aliquot samples from multiple primary samples in the form of a sample pretreatment system of which the configuration is shown in FIG. 7 and which pretreats samples for clinical laboratory tests prior to analyses. As shown in FIG. 8, this sample pretreatment system has one test tube placed on one holder for transfer purposes.

In this description, the term "sample(s)" refers to those liquid parts in a test tube, which are used for analyses by analyzers (e.g., serum and plasma obtained from blood through centrifuge).

In this description, the term "minimum guaranteed volume" refers to the volume of a sample expected to exist as a minimum in a test tube with a high degree of certainty. This is a value to be set for each test tube type.

A typical method for identifying the test tube type may involve reading a barcode or an RFID tag pasted on the test tube; processing an image taken of the test tube; or recognizing the color of the cap on the test tube.

The mode for carrying out this invention is in the form of a sample pretreatment system that pretreats samples for clinical laboratory tests prior to analyses, the system being capable of efficiently preparing multiple aliquot samples from multiple primary samples. For example, it is difficult to know the actual volume of the liquid in vacuum tubes because the quantity of the liquid varies from one vacuum tube to another due to the volume of each tube, the patient's blood pressure, and other factors. Also, although it is possible to measure the liquid volume in the tube, this requires installing an expensive, special liquid volume measuring device. The processing speed of this liquid volume measuring device is low, so that if the device is incorporated in the sample pretreatment system, the system will be not only expensive but also slow in its processing; this is not a practical solution.

In carrying out the present invention, a minimum guaranteed volume of the sample is set beforehand for each test tube type. A pipetting unit has each test tube type supplemented with the relevant minimum guaranteed volume when preparing aliquot samples from a primary sample. From the transferred test tubes, the pipetting unit prepares the largest possible number of aliquot samples in a manner not exceeding their minimum guaranteed volume.

For example, suppose that two test tubes containing a sample (primary sample) collected from a patient are input to the sample pretreatment system, that a pipetting request has been made to prepare four aliquot samples of 300 µL each from these primary samples, and that a minimum guaranteed volume of 1000 µL has been set for these test tubes. In that case, the pipetting unit prepares three aliquot samples from the first transferred test tube and a fourth aliquot sample from the next test tube having arrived. Generally, the details of the pipetting request are determined according to the type and number of test items, and a sufficient volume of a primary sample is collected to prepare as many aliquot samples as requested. Thus if all requested aliquot samples cannot be prepared from the primary samples having arrived at the pipetting unit, other primary samples are expected to arrive subsequently. On that assumption, regardless of the number of primary samples having arrived or the timing of their arrival, aliquot samples may be prepared successively from each arriving primary sample as in this mode of carrying out the invention and, upon arrival of the last primary sample, all requested aliquot samples are prepared. As outlined above, in carrying out the present invention, multiple aliquot samples can be prepared from multiple primary samples. There is no need to transfer multiple primary samples all at once, so that the decline of efficiency in other pretreatment processes such as the centrifuge process can be suppressed.

Also in the above example, suppose that the actual volume of the primary sample in the test tubes is 1100 µL and that an attempt is made to prepare four aliquot samples from the first transferred primary example. The fourth aliquot sample is then filled with less than 300 µL of the liquid (only 200 µL collected) and turns out to be a defective sample. In this case, the container used and the pipetting operation performed to prepare the fourth aliquot sample are wasted. By contrast, this mode of carrying out the invention eliminates such waste.

Also, starting from its initial value established by an operator, the minimum guaranteed volume of test tubes may be updated as needed to attain an appropriate value through the pipetting process repeated subsequently on the test tubes of the same type. Specifically, the primary sample left in a given test tube following preparation of aliquot samples may be entirely aspirated therefrom to prepare an archive sample that is saved in preparation for an urgent reexamination, for example. The aliquot volume of the aliquot samples prepared from the test tube and the aliquot volume of the archive sample are added up to obtain the actual measured value of the sample volume collected in the test tube in question. In this manner, the measured values are accumulated from each test tube, and the minimum guaranteed volume per test tube is updated on the basis of statistical data. Thus the validity of the minimum guaranteed volume is statistically enhanced, and so is the efficiency of preparing aliquot samples. As the population parameter increases, the reliability of the value is improved.

Furthermore, it might happen that following partial preparation of the aliquot samples to be pipetted, a predetermined time period elapses without the remaining aliquot samples being prepared. Such incidence may be reported to the operator by additional arrangements. For example, despite the total requested volume of aliquot samples, there may well be an insufficient volume of the primary sample having been collected. In such a case, the next primary sample is never transferred for the remaining aliquot samples to be prepared therefrom. When the next primary sample does not arrive and a predetermined time period has elapsed, the operator may be notified of the shortage of the primary sample. The operator is thus prompted to take measures such as additional collection of the primary sample.

Other additional arrangements may also be provided to reduce the wasteful use of consumables and the wastefully performed steps resulting from the preparation of more archive samples than are necessary. For example, it may be determined that the primary sample left unaspirated in each test tube is to be entirely aspirated to prepare an archive sample and that archive samples are to be prepared from all test tubes. In this case, as many archive samples as the number of the primary sample test tubes involved will be prepared unconditionally. Consequently, there may well be prepared numerous quantitatively insufficient archive samples for an eventual reexamination. In such cases, the containers used and the pipetting operations performed to prepare archive samples are wasted. To counter this waste, the minimum volume of the sample to be archived should be determined beforehand. The volume of the primary sample left in the test tubes following the preparation of aliquot samples is then estimated from the difference between the relevant minimum guaranteed volume and the volume pipetted to make aliquot samples. If the volume of the sample leftovers fails to meet the minimum volume of the archive sample, the archive sample will not be prepared. An archive sample is prepared only if at least the minimum volume of the archive sample is found to be met. This makes it possible to suppress the wasteful use of archive sample containers and the wastefully performed pipetting operations resulting from the preparation of archive samples.

Also, of the multiple test tubes of the primary sample, the test tube that has last arrived at the pipetting unit is generally left holding the largest volume of the primary sample subsequent to the preparation of aliquot samples. Consequently, only if the test tube from which the last of the requested aliquot samples has been pipetted contains a quantity of the leftover primary sample greater than the minimum volume of the archive sample, the archive sample can be prepared from that test tube, for example. That is, the archive sample may be prepared from the test tube from which the last aliquot sample has been pipetted. In this case, it is possible to avoid preparing multiple archive samples from the same primary sample and thereby to minimize the quantity of archive samples.

Incidentally, different types of multiple test tubes may be used to collect the same primary sample. Where multiple aliquot samples are to be prepared from such different types of test tubes, the examples below can also be applied.

Some embodiments of the present invention are explained below with reference to the accompanying drawings.

First Embodiment

The first embodiment of the present invention is explained below in detail with reference to the accompanying drawings.

Figure 1:
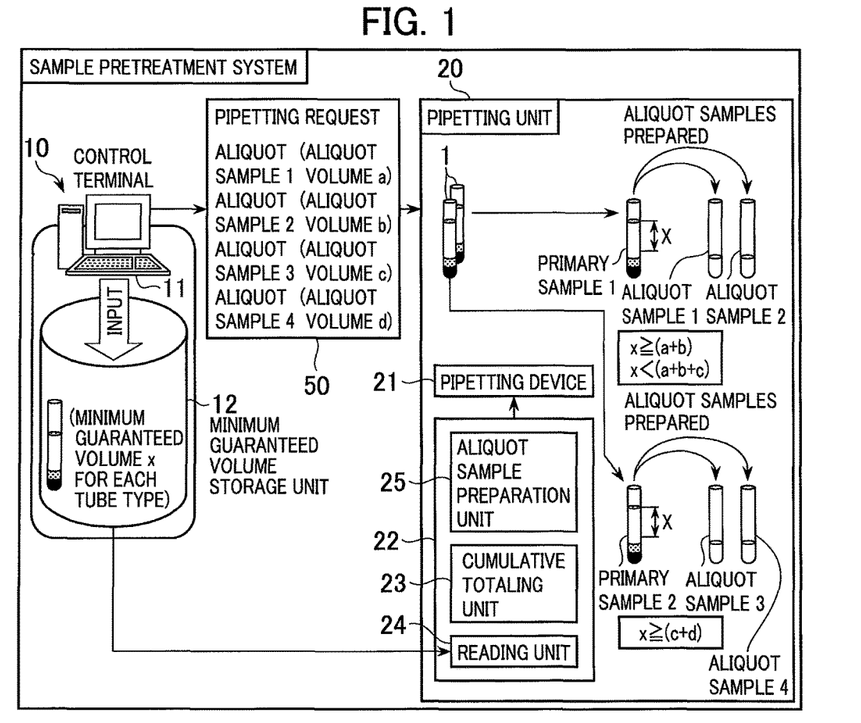
FIG. 1 is a block diagram of a sample pretreatment system as a first embodiment of the present invention, the diagram also illustrating the concept of the control involved.

FIG. 1 is a block diagram of a sample pretreatment system as the first embodiment of the present invention, the diagram also illustrating the concept of the control involved.

In FIG. 1, the sample pretreatment system includes a control terminal 10 and a pipetting unit 20. The control terminal 10 includes setting means 11 and a minimum guaranteed volume storage unit 12. The minimum guaranteed volume storage unit 12 stores the minimum guaranteed volume value set for each type of tubes as one example of test tubes. As mentioned above, the term "minimum guaranteed volume" refers to the volume of the sample expected to be held as a minimum in each target tube. The minimum guaranteed volumes are input by the operator operating the setting means 11 of the control terminal 10 for storage into the minimum guaranteed volume storage unit 12.

The pipetting unit 20 includes a pipetting device 21 and a control device 22 for use therewith. The pipetting device 21 is one of pretreatment devices. This sample pretreatment system includes at least the pipetting device 21 as its pretreatment device. The system may further include other pretreatment devices such as a centrifugal separator that separates samples centrifugally and a cap opening device that uncaps samples. The control device 22 includes a cumulative totaling unit 23, a reading unit 24, and an aliquot sample preparation unit 25. The cumulative totaling unit 23 is a processing unit that adds up the aliquot volumes of aliquot samples in the supplied tubes on the basis of pipetting request information 50. The pipetting request information 50 is input by the operator operating the setting means 11 and is transmitted from the control terminal 10 to the pretreatment units including the pipetting unit 20. (The pipetting request information 50 may also be transferred from a host computer to the control terminal 10 and to various pretreatment units.) The reading unit 24 reads from the minimum guaranteed volume storage unit 12 the minimum guaranteed volume of the tube of interest on the basis of the type of the tube fed to the pipetting device 21. A barcode reader (not shown) attached to the pipetting unit 20 reads the barcode (not shown) pasted on each tube for tube type identification. The aliquot sample preparation unit 25 compares the minimum guaranteed volume read by the reading unit 24 successively with the total cumulative value of the aliquot volumes of aliquot samples calculated by the cumulative totaling unit 23, and causes the pipetting device 21 to pipette the largest possible number of aliquot samples in a manner not exceeding the minimum guaranteed volume.

Figure 2:
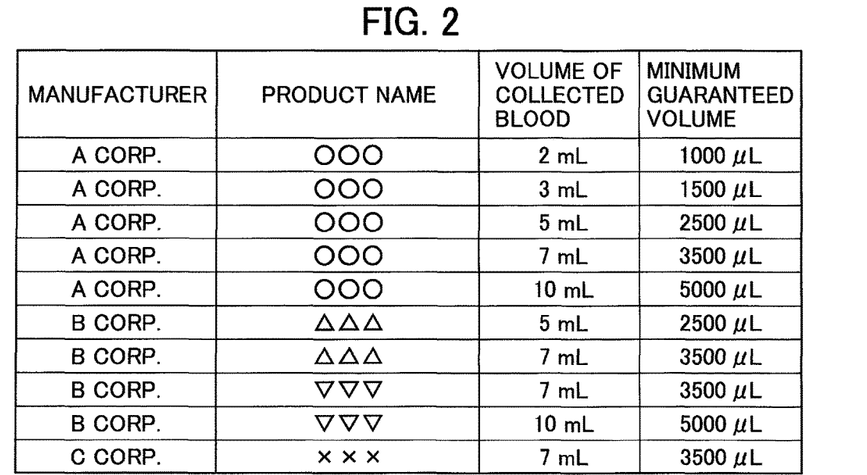
FIG. 2 is a tabular view showing a typical database of minimum guaranteed volumes stored in a minimum guaranteed volume storage unit.

FIG. 2 is a tabular view showing a typical database of minimum guaranteed volumes stored in the minimum guaranteed volume storage unit.

As shown in FIG. 2, with regard to the minimum guaranteed volume of each tube, the tubes may be classified by manufacturer, by product name, and by volume of collected blood. The term "manufacturer" refers to the entity that has produced the tubes; the term "product name" refers to the names given to the tubes by their manufacturer; and the term "volume of collected blood" refers to the volume of blood designated by the manufacturer for the tube of interest. For example, the type of a given tube may be distinguished as manufacturer A's tube named "ooo" having the volume of collected blood of 2 mL, or as manufacturer C's tube named "xxx" having the volume of collected blood of 7 mL. The tubes produced by the same manufacturer and given the same product name are still distinguished from one another if they have different volumes of collected blood. Thus manufacturer A's tubes named "ooo" are distinguished from one another if they have the volumes of collected blood of 2 mL, 3 mL, 5 mL, and 7 mL. The minimum guaranteed volume of a given tube is set to be lower than its volume of collected blood designated by the manufacturer. Listed here as an example are the minimum guaranteed volumes each set to be half the corresponding volume of collected blood of each tube type on the basis of the volume of centrifuged blood with a separating agent included in the blood cell components in relation to the volume of serum in the blood. Such identification information about the tubes is turned into a barcode pasted on each tube and is recognized by each of the pretreatment devices configured.

The operation of the sample pretreatment system as one embodiment of the present invention structured as described above is now explained below.

Suppose that four aliquot samples are needed of a patient's blood (each aliquot volume of the first through the fourth aliquot samples is assumed to be a to d). In this case, in keeping with the total aliquot volume of the first through the fourth aliquot samples, some (e.g., 2) tubes 1 are used to collect the primary sample from the patient. The tubes are each provided with information about the tube and the sample inside in the form of a barcode, and are input to the sample pretreatment system. The input tubes are subjected to other processes such as the centrifuge process before being transferred to the pipetting unit 20 by a transfer device (not shown).

The pipetting unit 20, on the basis of the information from the barcode pasted on the tube 1 that has first arrived, causes the reading unit 24 to read the minimum guaranteed volume set for the type of this tube 1 (alternatively, imaging means may be provided to acquire an external image of the tube 1 and the recognized external image may be used as the basis for reading the minimum guaranteed volume). It is assumed here that the minimum guaranteed volume of X is set for the tube 1. Also, the aliquot request information corresponding to the primary sample in the tube 1 of interest is read from the control terminal 10.

Next, the cumulative totaling unit 23 calculates successively the cumulative total values of the aliquot volumes a to d of the first through the fourth aliquot samples. Specifically, the values of a, (a+b), (a+b+c), and (a+b+c+d) are calculated in that order. If the aliquot volumes a to d are different from one another, these values may be rearranged in ascending order and their cumulative total values may be calculated successively. For example, if $a<c=d<b$, then the cumulative total values may be calculated in the order of a, (a+c), (a+c+d), and (a+c+d+b).

When the cumulative totaling unit 23 has calculated the cumulative total values of the aliquot volumes of the first through the fourth aliquot samples, the aliquot sample preparation unit 25 selects from these values the value that is closest to but smaller than the minimum guaranteed value X. The aliquot sample preparation unit 25 orders the pipetting device 21 to prepare the aliquot samples corresponding to the selected cumulative total value and in a manner not exceeding the minimum guaranteed volume X. If there is any aliquot sample yet to be prepared, another tube having the same primary sample collected therein is awaited. For example, suppose that the cumulative total values of a, (a+b), (a+b+c), and (a+b+c+d) have been calculated; that each of the values is compared with the volume X; and that the volume X is exceeded for the first time by the cumulative total value of (a+b+c). The value of (a+b) is then selected. In this case, the aliquot sample preparation unit 25 orders the pipetting device 21 to perform two pipetting operations involving the aliquot volumes "a" and "b" to prepare the first and the second aliquot samples. Information about the prepared aliquot samples is attached to the aliquot request information that is transmitted to the control terminal 10.

Later, when the second tube 1 having the same primary sample collected therein has arrived at the pipetting unit 20, the pipetting unit 20 performs the same process as that carried out on the first tube 1. That is, the pipetting unit 20 reads the minimum guaranteed volume X and the aliquot request information 50 from the control terminal 10, calculates the cumulative total values of the aliquot volumes of the third and the fourth aliquot samples, compares each of the values with the volume X, and orders the pipetting device 21 to prepare an available aliquot sample or samples accordingly. For example, if the minimum guaranteed volume X is not exceeded by the sum of the aliquot volumes "c" and "d" of the remaining third and fourth aliquot samples (X≥(c+d)), the aliquot sample preparation unit 25 orders the pipetting device 21 to perform two pipetting operations involving the aliquot volumes "c" and "d" to prepare the third and the fourth aliquot samples. Also, information about the third and the fourth aliquot samples having been prepared is attached to the aliquot request information that is to be transmitted to the control terminal 10.

As discussed above, this embodiment involves setting beforehand the minimum guaranteed volume of the sample in tubes for each tube type and, from the tubes arriving successively at the pipetting unit, preparing requested aliquot samples one after another in a manner not exceeding the corresponding minimum guaranteed volume. If not all requested aliquot samples can be prepared at once, another primary sample is expected to be transferred. The remaining aliquot samples are then prepared from the primary sample that will be transferred later. In this manner, multiple aliquot samples can be prepared efficiently from multiple primary samples regardless of the number of arriving primary samples or of their timing of arrival. There is no need to transfer multiple primary samples all at once, so that the efficiency of other pretreatment processes such as the centrifuge process is prevented from declining. Since there is no need to use special devices for measuring the volumes of collected primary samples, the rise in equipment cost can be suppressed. Furthermore, because the incidence of aliquot samples not meeting the requested aliquot volume (i.e., defective samples) is suppressed, the wasteful use of aliquot sample containers is reduced. At the same time, unnecessary pipetting operations are avoided so that the speed of processing is improved.

Second Embodiment

Figure 3:
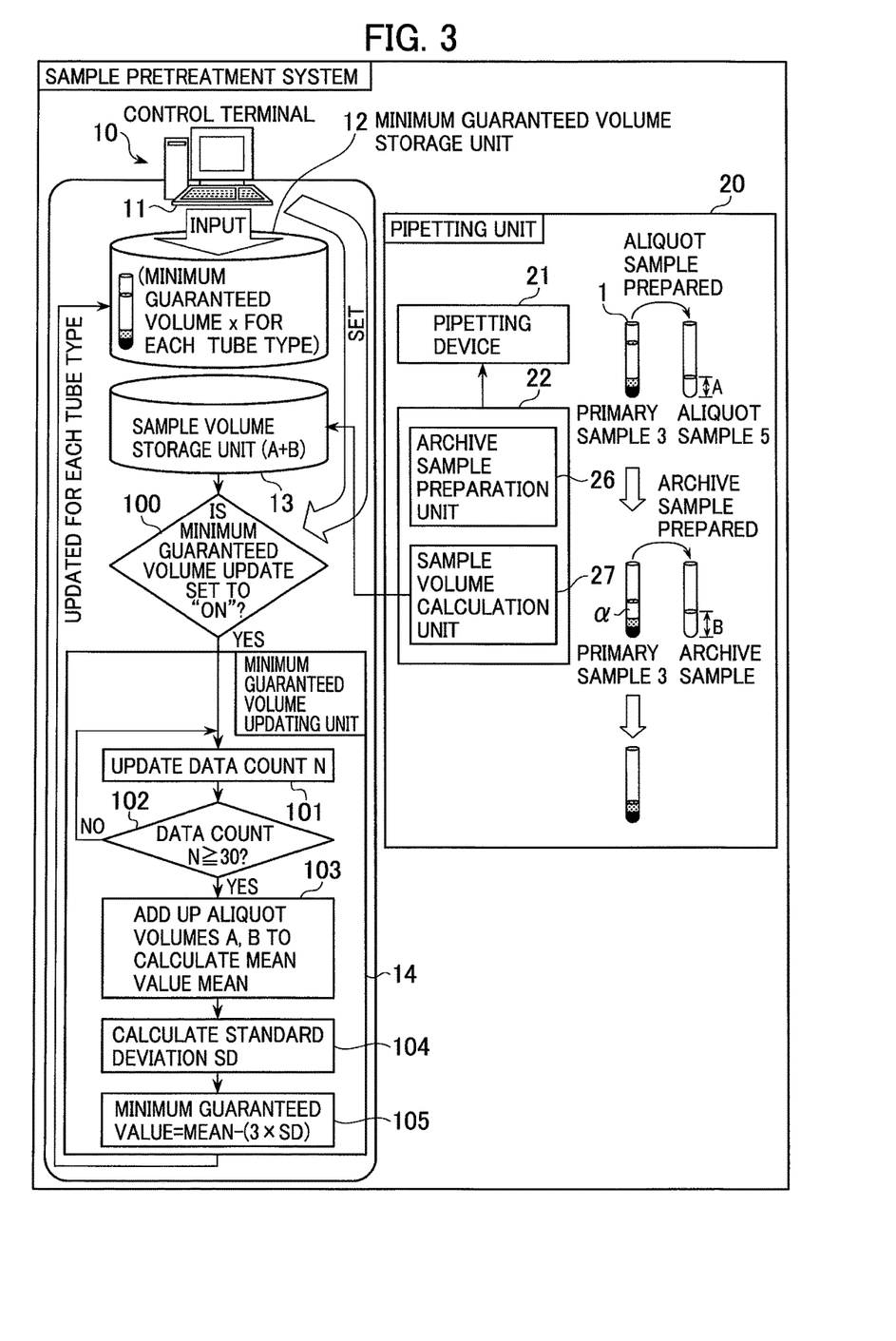
FIG. 3 is a block diagram of a sample pretreatment system as a second embodiment of the present invention, the diagram also illustrating the concept of the control involved.

FIG. 3 is a block diagram of a sample pretreatment system as the second embodiment of the present invention, the diagram also illustrating the concept of the control involved. This embodiment is configured by supplementing the configuration of the first embodiment with a sample volume storage unit 13, a minimum guaranteed volume updating unit 14, an archive sample preparation unit 26, and a sample volume calculation unit 27. In this embodiment, the sample volume storage unit 13 and minimum guaranteed volume updating unit 14 are built in the control terminal 10, and the archive sample preparation unit 26 and sample volume calculation unit 27 are incorporated in the control device 22 of the pipetting unit 20. The structures and the workings similar to those of the first embodiment will not be illustrated and/or discussed further where redundant.

The archive sample preparation unit 26 is an ordering unit that orders the pipetting device 21, following preparation of the aliquot samples under orders from the aliquot sample preparation unit 25, to aspirate entirely the primary sample left in the tube 1 and pipette the leftovers into another container to prepare an archive sample. With regard to the tube 1 used to prepare the archive example, the sample volume calculation unit 27 adds up the aliquot volumes of the prepared aliquot samples and the aliquot volume of the prepared archive sample, thereby calculating the volume of the sample collected originally in the tube 1 of interest (i.e., estimated volume of the primary sample in the tube before pipetting). The sample volume storage unit 13 is a storage unit that stores and accumulates for each tube type the sample volume values calculated by the sample volume calculation unit 27. The minimum guaranteed volume updating unit 14 is a processing unit that processes statistically for each tube type the sample volume values stored in the sample volume storage unit 13 and updates accordingly the corresponding minimum guaranteed volume values stored in the minimum guaranteed volume storage unit 12. The other structures are the same as those of the first embodiment.

The operation of this embodiment is now explained. For example, suppose that five aliquot samples are to be prepared from the primary sample collected from a given patient and that, following preparation of four aliquot samples from the first two tubes 1 of the primary sample in the same manner as in the first embodiment, the fifth aliquot sample is to be prepared from a third tube 1. How the first four aliquot samples are prepared is the same as in the first embodiment and thus will not be illustrated and/or discussed further.

First, upon arrival of the third tube 1, the reading unit 24, cumulative totaling unit 23, and aliquot sample preparation unit 25 in the pipetting unit 20 perform their processes to prepare the fifth aliquot sample from the third tube 1 in the same manner as in the first embodiment. Following preparation of the aliquot sample, the tube 1 has some primary sample (leftover α) left unaspirated as shown in FIG. 3. In this embodiment, the pipetting device 21 is ordered by the archive sample preparation unit 26 to aspirate entirely the primary sample leftover α and pipette it (the entire leftover α into another container) to prepare an archive sample. The sample volume calculation unit 27 adds up the total aliquot volume of the aliquot sample prepared from the third tube 1 (aliquot volume A of the fifth aliquot sample alone in this example) and the aliquot volume of the archive sample (aliquot volume B in this example). The sample volume calculation unit 27 transmits the sum of the aliquot volumes, along with the corresponding tube type information, to the control terminal 10 as the volume of the primary sample (sample volume) collected originally in the tube 1 (third tube 1) upon arrival at the pipetting unit 20. The control terminal 10 stores the sample volume information and the tube type information into the sample volume storage unit 13. In this manner, as the operation of the sample pretreatment system proceeds, the sample volume information is accumulated regarding each tube type in the sample volume storage unit 13.

While the sample pretreatment system is in operation, the minimum guaranteed volume updating unit 14 performs steps 101 through 105 below at predetermined time intervals or as needed.

(Step 101)

First, the sample volume data accumulated about a given tube type is read from the sample volume storage unit 13 and the number N of data items making up the sample volumes is updated. In this embodiment, performing the above-described process of archive sample preparation increments by 1 the number N of the sample volume data items about the tube 1 recognized earlier by the minimum guaranteed volume updating unit 14, and the data count N is updated to the value in effect following the increment.

(Step 102)

The data count N is then compared with a threshold value (30 in this example, to be changeable). Specifically, it is determined whether the data count N is equal to or larger than 30. If the data count N is determined to be less than 30, a data shortage is recognized. Control is then returned to step 101 and remains in this step until the data count of 30 is attained. On the other hand, if it is determined in step 102 that the data count N is 30 or larger, control is passed to step 103.

(Steps 103-105)

A process is carried out to calculate a mean value MEAN of the sample volume data of which the data count is at least 30 (step 103). A standard deviation SD of the sample volume data is further calculated (step 104). Since experience shows that the volumes of the primary sample collected in tubes (i.e., sample volume) approximately obey normal distribution, the sample volume may be considered to fall within the mean value MEAN±(3×SD). Consequently, the value of {MEAN−(3×SD)} is calculated as the new minimum guaranteed value (step 105).

Figure 4:
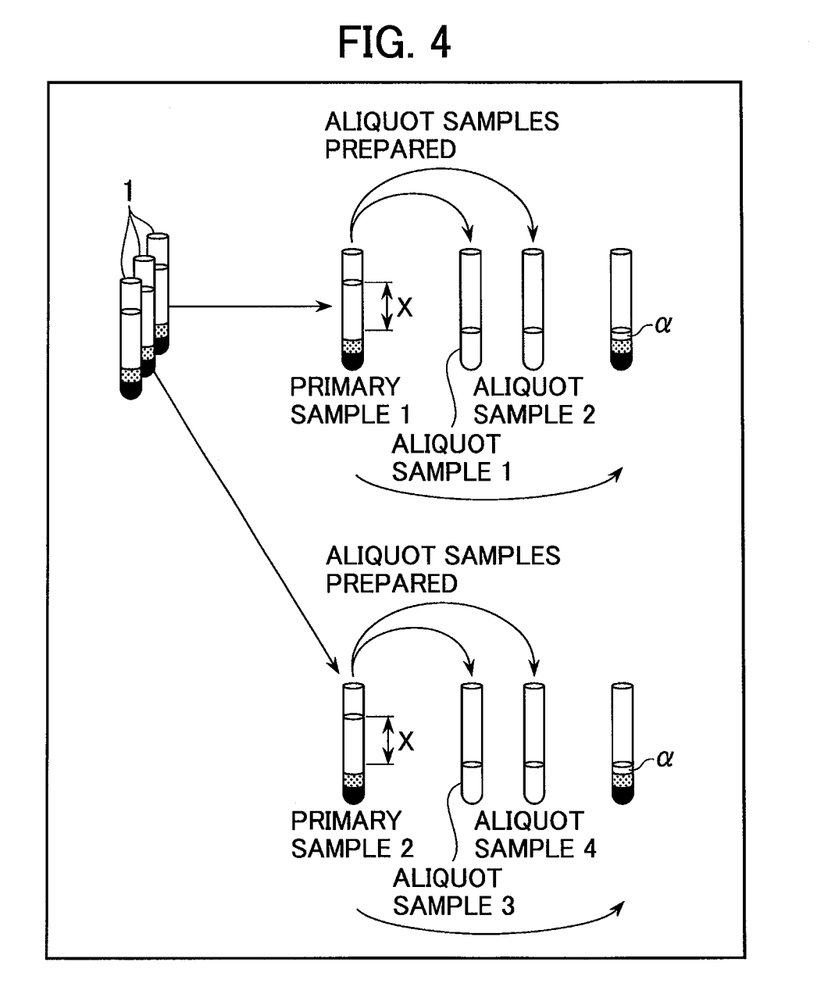
FIG. 4 is a diagram explaining the leftovers of a primary sample in tubes after preparation of aliquot samples.

The minimum guaranteed volume updating unit 14 transmits the minimum guaranteed volume value thus calculated to the minimum guaranteed volume storage unit 12, replacing the minimum guaranteed volume currently set for the tube type of interest with the newly calculated value. By repeating the above steps, the minimum guaranteed volume updating unit 14 keeps updating the minimum guaranteed volume data for each tube type in the minimum guaranteed volume storage unit 12.

Where the primary sample of the tube 1 is to be pipetted to make multiple aliquot samples, there may be some primary sample left unaspirated in the tube 1, as shown in FIG. 4, following preparation of the aliquot samples depending on the relations between the actual volume of the primary sample collected in the tube 1 on the one hand and the aliquot volumes of the aliquot samples on the other hand. The leftover α should preferably be as limited as possible. Thus in this embodiment, the archive sample preparation process is performed as described above. The aliquot volume of the archive sample is added to the aliquot volume resulting from the aliquot sample preparation process (added to the sum of the aliquot volumes if multiple aliquot samples have been prepared from the same tube 1) carried out earlier on the tube 1. The addition calculates the volume of the sample collected in the tube 1, and the sample volume value thus calculated is stored into the sample volume storage unit 13. When a predetermined number of data items about the same tube type have been obtained, these data items are statistically processed to update the settings of the minimum guaranteed volumes. In this manner, in addition to the benefits of the first embodiment, the second embodiment offers the benefit of enhanced accuracy and reliability of the minimum guaranteed volume settings. This makes it possible to suppress excess leftovers a resulting from an unnecessarily low estimate of the minimum guaranteed volume with regard to the volume of the sample actually collected in the tube 1. As a result, the efficiency of preparing aliquot samples is improved, and the waste of the primary sample is diminished.

For the second embodiment, an example was shown above in which the archive sample is prepared only from the third of the three tubes 1. Alternatively, the archive sample may be prepared from each of all tubes supplied. In this case, the data count N can be raised higher, which further improves the reliability of the minimum guaranteed volumes.

Also in the second embodiment, if it is determined that the reliability of the minimum guaranteed volumes is sufficiently high, the update of the minimum guaranteed volumes on the control terminal 10 may be set from "ON" to "OFF." This allows a determining step 100 to disable the processing of the minimum guaranteed volume updating unit 14 thereby stopping the update of the minimum guaranteed volumes.

Third Embodiment

Figure 5:
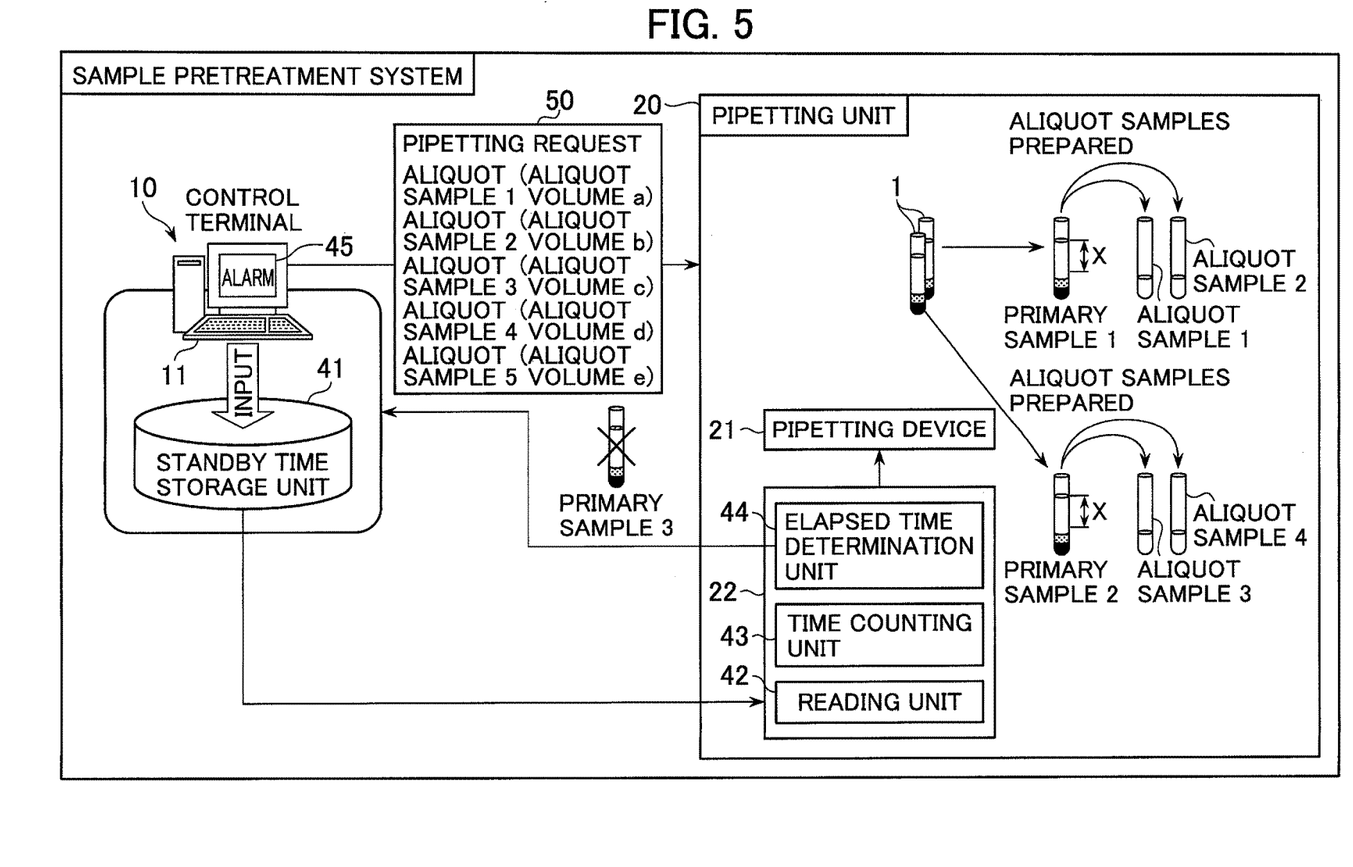
FIG. 5 is a block diagram of a sample pretreatment system as a third embodiment of the present invention, the diagram also illustrating the concept of the control involved.

FIG. 5 is a block diagram of a sample pretreatment system as the third embodiment of the present invention, the diagram also illustrating the concept of the control involved.

The third embodiment is configured by supplementing the configuration of the first or the second embodiment with notification means for notifying the operator of a primary sample shortage. Specifically, as shown in FIG. 5, the third embodiment includes a standby time storage unit 41, a reading unit 42, a time counting unit 43, and an elapsed time determination unit 44. The standby time storage unit 41 is built in the control terminal 10; and the reading unit 42, time counting unit 43, and elapsed time determination unit 44 are incorporated in the control device 22 of the pipetting unit 20. The structures and the workings similar to those of the above-described embodiments will not be illustrated and/or discussed further where redundant.

The standby time storage unit 41 is a storage unit that stores the standby time as the time period for determining whether or not to notify the operator of an abnormality. The standby time is the time period upon elapse of which no more tube 1 is expected to arrive bringing the primary sample requested to be pipetted. The standby time is input by the operator operating the setting means 11 in consideration of the processing speed and other factors of the sample pretreatment system. A different standby time may be set for each tube type. Alternatively, a common standby time may be set regardless of the tube type. The reading unit 42 is a functional unit that reads from the standby time storage unit 41 standby time data about the primary sample requested to be pipetted. The time counting unit 43 is a functional part that counts the elapsed time since the preparation of an aliquot sample out of a given primary sample.

Figure 9:
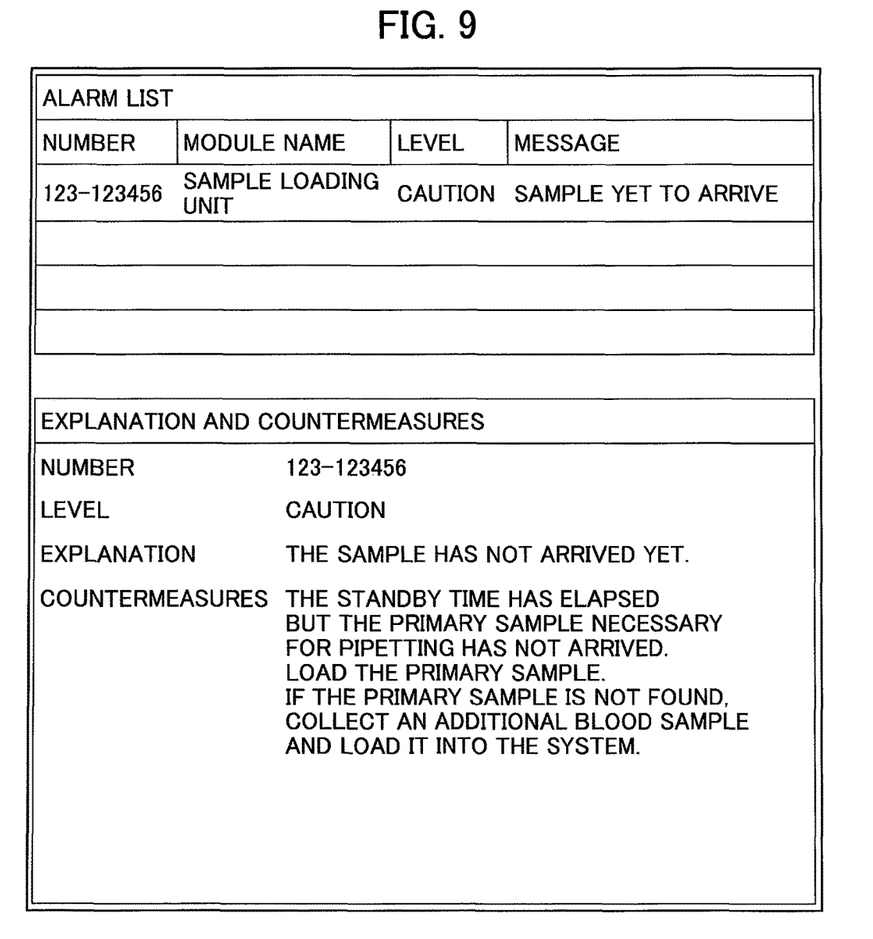
FIG. 9 is an illustration of a typical alarm display associated with the third embodiment of the present invention.

The elapsed time determination unit 44 is an estimation unit that determines whether the elapsed time counted by the time counting unit 43 with regard to a given primary sample has exceeded the standby time. If it is determined that the standby time is exceeded by the elapsed time since the preparation of part of aliquot samples from the primary sample in question has been started and before the preparation of all aliquot samples (unprepared remaining aliquot samples) requested of the primary sample is completed, the elapsed time determination unit 44 generates an alarm signal and sends it to the control terminal 10. Given the alarm signal, the control terminal 10 generates a display signal causing a display unit 45 of the control terminal 10 to display an alarm such as "The primary sample has not arrived" or "There is a shortage of the primary sample" with regard to the primary sample of interest, thus notifying the operator of the abnormality. FIG. 9 shows a typical alarm display. The notification is made not only in such text form but also with a warning by voice, an audible alert, a warning lamp or other means. These means may also be combined in a suitable manner. The other structures are the same as those of the first or the second embodiment.

With the third embodiment, suppose that an aliquot sample preparation request 50 has been made as shown in FIG. 5 to prepare five aliquot samples from the tube 1 arriving at the pipetting unit 20; that the reading unit 24, cumulative totaling unit 23, and aliquot sample preparation unit 25 have performed their processes to prepare two aliquot samples from the first tube 1; and that two more aliquot samples have been prepared from the next tube 1 having arrived before the standby time elapses. In this case, when the preparation of the fourth aliquot sample is completed, the time counting unit 43 starts counting time, and the elapsed time determination unit 44 compares the time counted by the time counting unit 43 with the standby time read by the reading unit 42. When the counted time is found eventually to exceed the standby time, an alarm signal is transmitted to the control terminal 10. In this manner, the operator is notified of a shortage of the primary example. In addition to the benefits similar to those of the first or the second embodiment, the third embodiment offers the benefit of notifying the operator of a primary sample shortage so that the operator may consider taking necessary measures such as additional collection of the primary sample in a timely manner.

Fourth Embodiment

Figure 6:
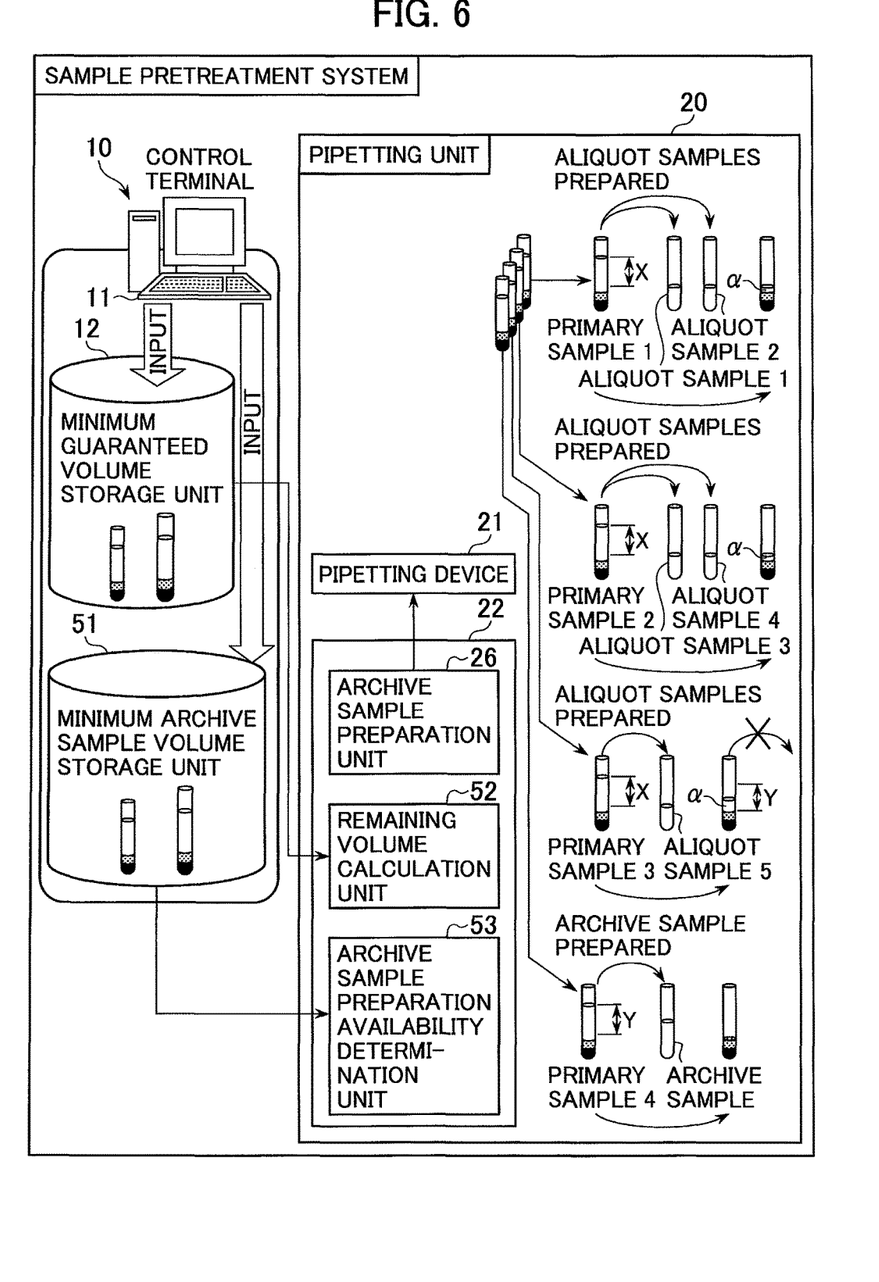
FIG. 6 is a block diagram of a sample pretreatment system as a fourth embodiment of the present invention, the diagram also illustrating the concept of the control involved.

FIG. 6 is a block diagram of a sample pretreatment system as the fourth embodiment of the present invention, the diagram also illustrating the concept of the control involved.

The fourth embodiment is configured by supplementing the configuration of the second embodiment with a minimum archive sample volume storage unit 51, an archive sample preparation unit 26, a remaining volume calculation unit 52, and an archive sample preparation availability determination unit 53 shown in FIG. 6. The minimum archive sample volume storage unit 51 is built in the control terminal 10; and the archive sample preparation unit 26, remaining volume calculation unit 52, and archive sample preparation availability determination unit 53 are incorporated in the control device 22 of the pipetting unit 20. The structures and the workings similar to those of the second embodiment will not be illustrated and/or discussed further where redundant.

The minimum archive sample volume storage unit 51 is a storage unit that stores the minimum archive sample volume value for each tube type. The minimum archive sample volume refers to the sample volume to be secured as a minimum in preparing an archive sample. As such, the minimum archive sample volume is prescribed for each tube type.

The remaining volume calculation unit 52 is a processing unit that calculates the remaining volume of the primary sample in the tube 1 transferred to the pipetting device 21 (volume of the leftover $\alpha$), by subtracting the aliquot volumes aspirated from the tube 1 in question and pipetted to make the aliquot samples, from the minimum guaranteed volume updated by the minimum guaranteed volume updating unit 14 with regard to the tube 1.

The archive sample preparation availability determination unit 53 compares the remaining volume of the primary sample calculated by the remaining volume calculation unit 52 with the minimum archive sample volume read from the minimum archive sample volume storage unit 51, and outputs a signal ordering the archive sample preparation unit 26 to prepare an archive sample only if the remaining volume of the primary sample is greater than the minimum archive volume. If the remaining volume of the primary sample turns out to be less than the minimum archive volume, the archive sample preparation availability determination unit 53 does not output the signal ordering the archive sample preparation unit 26 to prepare the archive sample.

The other structures are similar to those of the second embodiment.

In the fourth embodiment, once the preparation of aliquot samples is completed, the remaining volume calculation unit 52 calculates the remaining volume of the primary sample in the tube 1 on the basis of the aliquot volumes and the minimum guaranteed volume read from the minimum guaranteed volume storage unit 12. Because the minimum guaranteed volume used here has been updated by the minimum guaranteed volume updating unit 14 and is more reliable, the remaining volume of the primary sample can be calculated with high accuracy. The archive sample preparation availability determination unit 53 compares the remaining volume of the primary sample calculated by the remaining volume calculation unit 52 with the minimum archive sample volume read from the minimum archive sample volume storage unit 51, so as to determine whether or not to prepare an archive sample.

For example, suppose that, in preparing five aliquot samples from a given primary sample as shown in FIG. 6, two aliquot samples are prepared from each of the first two tubes 1 and the last (fifth) aliquot sample is prepared from the third tube 1. In this case, the remaining volume calculation unit 52 calculates the remaining volume of the primary sample in the third tube 1, and the archive sample preparation availability determination unit 53 determines whether or not to prepare an archive sample (although this process could also be performed on the first two tubes 1, it is assumed here that following the pipetting of two aliquot samples, the remaining volume in the tubes fell short of the minimum archive sample volume). In this example, as shown in FIG. 6, the remaining volume of the primary sample (leftover $\alpha$) following preparation of the aliquot sample from the third tube is assumed to fall short of a minimum archive sample volume Y. Then the archive sample preparation availability determination unit 53 completes the pipetting operation on the third tube 1 without outputting the signal ordering the archive sample preparation unit 26 to prepare the archive sample. That is, the preparation of an archive sample from the leftover $\alpha$ in the third tube 1 is avoided. If a fourth tube 1 does not eventually arrive at the pipetting unit 20, the archive sample of the primary sample in question will not be prepared. If the remaining volume of the primary sample in the third tube 1 is greater than the minimum archive sample volume Y, the archive sample preparation availability determination unit 53 outputs the signal ordering the archive sample preparation unit 26 to prepare an archive sample. With the archive sample prepared, the archive sample preparation availability determination unit 53 completes the pipetting operation on the third tube 1.

Still, as shown in FIG. 6, when the fourth tube 1 arrives eventually at the pipetting unit 20, the same process as discussed above is carried out. In this case, after aliquot sample preparation is performed zero times, the aliquot volume resulting from the preparation is zero. Thus the remaining volume of the primary sample becomes equal to the minimum guaranteed volume. As a result, more primary sample than the minimum archive sample volume Y is left in the fourth tube 1. The archive sample preparation availability determination unit 53 then outputs the signal ordering the archive sample preparation unit 26 to prepare an archive sample. The primary sample in the fourth tube is therefore all pipetted to make the archive sample.

In this manner, in addition to the benefits similar to those of the second embodiment, the fourth embodiment offers the benefit of avoiding the wasteful preparation of an archive sample, thereby reducing the use of consumables such as aliquot sample containers and barcode labels and eliminating wasteful pipetting operations.

Whereas the processing of the fourth embodiment is performed on the tubes 1 having arrived at the pipetting unit 20 as described above, it is also possible to carry out the processing of this embodiment only on the tube 1 from which the last requested aliquot sample was pipetted or solely on the tube 1 that has arrived separately after the preparation of the requested aliquot samples was completed. Needless to say, the fourth embodiment can be combined with the first or the third embodiment.

DESCRIPTION OF REFERENCE CHARACTERS

1: Tube (test tube)
11: Setting means
12: Minimum guaranteed volume storage unit
13: Sample volume storage unit
14: Minimum guaranteed volume updating unit
21: Pipetting device
23: Cumulative totaling unit
24: Reading unit
25: Aliquot sample preparation unit
26: Archive sample preparation unit
27: Sample volume calculation unit
45: Display unit (notification means)
50: Pipetting request information
51: Minimum archive sample volume storage unit
52: Remaining volume calculation unit
54: Archive sample preparation availability determination unit

The invention claimed is:

1. A sample pretreatment system comprising:
   a test tube containing a primary sample and having barcode information thereon;
   a pipetting device configured to pipette one or more aliquot samples from the primary sample contained in the test tube;
   a barcode reader configured to read the barcode information on the test tube; and
   a control device connected to the pipetting device and the barcode reader,
   wherein the control device stores minimum guaranteed volume information for each of a plurality of types of test tubes, the minimum guaranteed volume information indicating the minimum volume of sample guaranteed to be contained in the corresponding type of test tube,
   wherein the control device is programmed to:
   control the barcode reader to read the barcode information from the test tube,
   determine the type of the test tube based on the barcode information read by the barcode reader,
   determine the minimum guaranteed volume based on the type of the test tube,
   read in pipetting request information from a computer, the pipetting request information including a volume amount of each of a plurality of aliquot samples to be pipetted for the primary sample,
   determine a combination of aliquot samples of the plurality of aliquot samples in the pipetting request information to be pipetted from the primary sample contained in the test tube such that the cumulative volume of each of the volumes of the combination of the aliquot samples does not exceed the minimum guaranteed volume of the test tube, and
   control the pipetting device to only pipette the aliquot samples of the determined combination of the aliquot samples into respective aliquot sample containers.

2. The sample pretreatment system according to claim 1, further comprising
   a display,
   wherein the control device is further programmed to:
   determine whether an elapsed time from pipetting by the pipetting device of a part of all of the plurality of aliquot samples requested in the pipetting request information has exceeded a predetermined time, and
   upon determining the elapsed time has exceeded the predetermined time, control the display unit to display a notification.

3. The sample pretreatment system according to claim 1, further comprising:
   an archive sample container,
   wherein the control device is further programmed to:
   after all of the aliquot samples in the pipetting request information are pipetted by the pipette device from the test tube containing the primary sample, control the pipetting device to pipette a first remaining volume of primary sample from the test tube into the archive sample container,
   calculate a total sum volume which is the sum of each of the volumes of the aliquot samples of the combination of the aliquot samples and the first remaining volume,
   store the total sum volume in association with the test tube type, and
   upon determining a number of the total sum volumes for the test tube type is greater than or equal to a predetermined value, determine the mean total sum value for the test tube type based on the total sum volumes for the test tube type and store the mean total sum value as the minimum guaranteed volume for the corresponding test tube type.

4. The sample pretreatment system according to claim 3, wherein the control device is further programmed to:
   store a minimum volume value of the archive sample for each test tube type;
   calculate a second remaining volume of the primary sample remaining in the test tube by subtracting the aliquot volumes pipetted from the test tube from the minimum guaranteed volume,
   compare the second remaining volume of the primary sample the minimum volume of the archive sample and, only if the remaining volume is greater than the minimum volume of the archive sample, control the pipetting unit to pipette an aliquot sample from the archive sample.

5. The sample pretreatment system according to claim 1, further comprising a display, wherein the control device is further programmed to:

determine whether a total volume of each of the volume amounts for each of the plurality of aliquot samples requested in the pipetting request information is greater than the minimum guaranteed volume of the test tube type, and upon determining the total volume is greater than the minimum guaranteed volume, control the display to display a notification the total aliquot volumes of the aliquot samples is greater than the minimum guaranteed volume of the test tube containing the primary sample.

* * * * *